(12) United States Patent
Perricone

(10) Patent No.: US 6,908,941 B2
(45) Date of Patent: Jun. 21, 2005

(54) HAIR AND NAIL TREATMENTS USING ALKANOLAMINES

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 532 days.

(21) Appl. No.: 10/180,412

(22) Filed: Jun. 26, 2002

(65) Prior Publication Data

US 2004/0081634 A1 Apr. 29, 2004

(51) Int. Cl.[7] ..................... A61K 31/385; A61K 31/20; A61K 31/195; A61K 31/13; A61K 7/04
(52) U.S. Cl. ..................... 514/440; 514/558; 514/561; 514/667; 424/61; 424/70.1
(58) Field of Search ................ 514/440, 558, 514/561, 667; 424/61, 70.1

(56) References Cited

U.S. PATENT DOCUMENTS

| 5,554,647 A | 9/1996 | Perricone |
|---|---|---|
| 5,709,868 A | 1/1998 | Perricone |
| 5,965,618 A | 10/1999 | Perricone |
| 6,319,942 B1 | 11/2001 | Perricone |

OTHER PUBLICATIONS

Sahl, W.J., and Clever, H., Internat. J. Derm., 1994, 33: 681–691 (part I) and 763–769 (part II).
Sen, C.K., et al., Free Radical Biol. Med., 1998, 25:89.

*Primary Examiner*—Raymond J. Henley III
(74) *Attorney, Agent, or Firm*—St. Onge Steward Johnston & Reens LLC

(57) ABSTRACT

Topical application of compositions containing an alkanolamine such as dimethylaminoethanol increase smoothness and surface uniformity of hair and nails and enhances hair and nail growth. Application to the hair and underlying skin areas containing the hair bulbs, fingernails or toenails and paraungual areas containing the nail matrices increases the elasticity and enhances the luster of hair and nails, provides emolliency to their keratin matrix, and quells inflammation to promote superior keratin formation. Alkanolamine compositions contain at least one other adjunct ingredient such as tyrosine, lipoic acid, folic acid, an α-hydroxy acid, or a fatty acid ester of ascorbic acid in most embodiments to augment beneficial effects of the treatments.

20 Claims, No Drawings

HAIR AND NAIL TREATMENTS USING ALKANOLAMINES

CROSS-REFERENCES TO RELATED APPLICATIONS

This application claims priority benefit and is a 371 of PCT/US02/18026, filed internationally in the US/RO on 6 Jun. 2002.

BACKGROUND OF THE INVENTION

1. Field of the Invention

This invention relates to compositions and methods for improving the appearance and health of hair and nails, the emolliency of keratin in hair and nails, and the production of more uniform keratin by the hair bulb and nail matrix.

2. Background of the Invention

As evidenced by the many ancient descriptions of nail and hair treatments and remedies for baldness, the desire to have and retain healthy-looking hair and nails has been important to mankind for thousands of years. In modern times, a huge industry is devoted to optimizing the amount of hair we have and the quality of the tresses, and nail beautification treatments.

Each hair grows from a follicle in the skin, which generally develops at an angle to the skin surface. At its base is the hair bulb, from which the hair itself actually grows. In the hair follicle is a sebaceous gland, which produces (sebum) oil that lubricate the hair and skin as well, an erector pili muscle, and capillaries that nourish the hair. The actual hair shaft develops from active cells in the center portion of the hair bulb. The sheaths and contained hair are derived from the hair bulb and form hair as concentric cylindrical layers of hard keratin, a highly insoluble fibrous scleroprotein which is also the principal constituent of nails.

Nails grow as an extrusion from a nail matrix just under the cuticle on the dorsal surface of the distal ends of the fingers and toes. Since fingernails especially, but also toenails, are in constant contact with the environment, they are subjected to a great deal of minor and sometimes major trauma. The tough nature of keratin is such that damaged hair and brittle nails are hard to treat. It would therefore be desirable to have new and improved treatments for hair and nails, to render them smoother, softer, more lustrous and elastic, and healthier-looking.

BRIEF SUMMARY OF THE INVENTION

It is a primary objective of the invention to provide a composition that can be used topically to improve the appearance of hair and nails, rendering them more uniform and smoother. It is a more specific objective of the invention to add emolliency to the keratin matrix of hair and nails, and to provide the production of superior keratin by the hair bulb and nail matrix, promoting good hair growth and nicer nail plates.

These and other objectives are accomplished by this invention, which provides topical compositions containing an alkanolamine such as ethylaminoethanol, methylaminoethanol, dimethylaminoethanol, isopropanolamine, triethanolamine, isopropanoldimethylamine, ethylethanolamine, 2-butanolamine, choline, serine, and mixtures thereof, which are applied to hair and underlying skin areas, i.e., the skin containing hair roots and bulbs such as the scalp, and to nails and the paraungual regions of nails, especially the skin above the matrix for the nail plate, to render hair and nails more uniform and smoother, to stimulate the production of more uniform keratin, and to treat subclinical and clinical inflammation in and around the hair bulbs and nail matrices. Dimethylaminoethanol is particularly preferred. Amounts of active alkanolamine ingredient range from about 0.1 to about 10%, more narrowly from about 1% to about 3%, by weight of the total composition. Adjunct ingredients such as tyrosine, lipoic acid, folic acid, a fatty acid ester of ascorbic acid, e.g., ascorbyl palmitate, and/or an α-hydroxy acid, e.g., glycolic acid, may be added to formulations of the invention. Treated hair becomes softer, shinier and more manageable, and nails become less brittle and more lustrous. Pronounced cosmetic benefits are achieved.

BRIEF DESCRIPTION OF THE INVENTION

This invention is based upon the finding that application of alkanolamines to hair and nails has a similar effect on keratin as what has been observed with collagen, while simultaneously providing to surrounding skin areas, the beneficial effects of topical alkanolamine treatments.

Alkanolamine compositions have previously been suggested for the treatment of cutaneous scars (U.S. Pat. No. 6,319,942 to Perricone; this and other references cited hereafter are hereby incorporated herein in their entireties). Scars result from wound healing, which occurs in three separate phases: inflammation, formation of granulation tissue, and matrix formation. (For a review, see Sahl, W. J., and Clever, H., *Internat. J. Derm.*, 1994, 33: 681–691 (part I) and 763–769 (part II)). While not wishing to be bound to any theory, alkanolamines appear to be beneficial in scar treatments, particularly for the treatment of hypertrophic and keloid scars, in all three phases. During the first phase, damage to endothelial cells, complement, and platelets at the wound site release chemotactic factors that result in the infusion of neutrophils, lymphocytes and macrophages, which aids in the removal of infection and foreign debris. As in all inflammatory processes, there is generation of free radicals, which damages cell membranes and results in formation of oxidized proteins and fats, and cross-linked new collagen, laying a scaffold for the next phase.

At the end of the inflammatory phase, the granulation phase begins with an influx of fibroblasts and endothelial cells to the wound. Other key cells in this phase are macrophages and platelets. Macrophages induce the beginning of granulation by relasing platelet-derived growth factor (PDGF), tumor necrosis growth factor (TGF)-α, and an epidermal growth factor-like substance. Activated platelets release epidermal growth factor (EGF), PDGF, TGF-α, and TGF-β. Together these play roles in the re-epithelialization process wherein keratinocytes cells migrate in sheaths over a provisional matrix consisting primarily of fibrin, fibronectin, type V collagen, and tenascin, and produce their own fibronectin receptors.

Once re-epithelilization has occurred, keratinocytes resume their normal differentiated form, and matrix formation begins. Matrix formation consists primarily of the construction of derma matrix, which is regulated by fibroblasts. Chemotaxis of fibroblasts results in the production of abundant quantities of hyaluronate, fibronectin, and types I and III collagen. These components comprise the bulk of the provisional extracellular matrix in the early part of this wound repair phase. Hyaluronic acid (HA) creates an open-weave pattern in the collagen/fibronectin scaffold, facilitating fibroblast movement. HA production falls after about the fifth day of wound healing, and levels of chronroitin sulfate in dermatan sulfate increase. Fibronectin deposits in the collagen, and wound contraction begins. Biochemically during the contraction stage, hyaluronidase and proteinase are present, type I collagen synthesis is stimulated, and increased levels of chronroitin sulfate, dermatin sulfate and proteoglycans are observed; together these restructure the matrix. At the end of the healing process, the final scar shows collagen fibers mostly parallel to the epidermis.

Again, while not wishing to be bound to any theory, alkanolamines seem to exert similar effects in the hair follicle and nail matrix, and on the keratin itself. Hair shafts tend to become dull, brittle and rough primarily as a result of carbonyl formation in the keratin. Nail plates likewise become dried and cracked. Alkanolamines are natural penetrants that simultaneously act as antioxidants and emollients within the keratin matrix, making hair and nails softer, shinier, smoother, and more elastic. At the same time, alkanolamines penetrate the scalp and other skin areas containing hair bulbs, and the paraungual areas of nails, promoting the production of smoother and superior keratin formation. Most persons have subclinical if not clinical inflammation in and around hair bulbs and the dermis matrix for nail plates since hair and nails are continuously subjected to physical and chemical trauma as a result of being exposed constantly to the environment, as well as presenting occasionally with more extreme pathological conditions as a result of cuts and scrapes, infection, dermatitis, seborrhea, and the like. This inflammation results in less than perfect keratin formation. Alkanolamines are natural anti-inflamrnatories that promote better growth of the hair shaft and the formation of nicer nail plates.

In the practice of the invention, compositions that contain an effective amount of an alkanolamine of the formula

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group, are topically applied to hair or nails to render them more uniform and smoother and to surrounding skin areas to quell inflammation in the hair bulb and nail matrix region, promoting superior keratin formation. As used herein, the term "nail" includes either fingernails or toenails, or both. Useful compounds for the invention include, but are not limited to, ethylaminoethanol, methylaninoethanol, dimethylaminoethanol, isopropanolamine, triethanolamine, isopropanoldimethylamine, ethylethanolamine, 2-butanolamine, choline, serine, and mixtures thereof. Many preferred embodiments employ methylaminoaminoethanol, dimethylaminoethanol, ethylaminoethanol, and/or triethanolamine; particularly preferred is dimethylaminoethanol (DMAE).

The amount of alkanolamine necessary to treat hair or nails is not fixed per se, and necessarily is dependent upon the identity of alkanolamine employed, the amount and type of other active and adjunct ingredients employed, the user's hair and nail type, and the severity and extent of the conditions treated. Most compositions of the invention contain from about 0.1% to about 10% by weight, more narrowly from about 0.25% to about 5% to 7% by weight, and in many cases from about 1% to about 3% by weight, alkanolamine such as dimethylaminoethanol in the total composition, typically in association with a dermatologically acceptable carrier more fully described below. In some examples that follow, efficacious compositions illustrating the invention contain from about 2% to 3% DMAE.

Many alkanolamine compositions of the invention contain at least one adjunct ingredient. Adjunct ingredients include, but are not limited to, tyrosine, lipoic acid, folic acid, α-hydroxy acids, fatty acid esters of ascorbic acid, and vitamin A and vitamin A derivatives. Many embodiments employ more than one adjunct ingredient. Where employed, adjunct ingredients have additive effects if not synergistic effects due to different mechanisms of action.

Alkanolamine compositions of the invention that comprise tyrosine typically are formulated to contain from about 0.01% to about 6%, more narrowly from about 0.03% to about 5% by weight, and, in many embodiments, from about 0.2% to about 3% by weight tyrosine, based on the total composition. Compositions illustrated in the examples that follow contain from 0.1 to 5% tyrosine.

Lipoic acid is an adjunct ingredient in many embodiments. The term "lipoic acid" encompasses thioctic acid (1,2-dithiolane-3-pentanoic acid; 1,2-dithiolane-3-valeric acid), $C_8H_{14}O_2S_2$, formula weight 206.32, and its reduced form, dihydrolipoic acid. It has been variously known as acetate replacing factor, protogen A, and pyruvate oxidation factor. As mentioned above, for convenience, as used herein, where the properties and advantages of "lipoic acid" (or LA) are discussed as an adjunct ingredient in the practice of the invention, both lipoic acid and its derivatives are encompassed. "Lipoic acid derivatives" include thioctic acid esters, particularly alkyl esters such as fatty acid esters, amides, particularly those isolated from or mimicking naturally occurring lipoamides, salts, particularly alkali metal salts, anhydrides and specifically includes the reduced form, dihydrolipoic acid and its esters, amides and salts. One particularly efficacious derivative that exhibits increased cellular uptake and biological activity useful in the practice of the invention is N,N-dimethyl, N-2-amidoethyl lipoate described by Sen, C. K., et al. (*Free Radical Biol. Med.,* 1998, 25; 89) and called lipoic acid plus (LA-Plus). Since lipoic acid is both fat- and water-soluble, it is an advantage of the invention that it can be used in either lipid or aqueous-based compositions, and it readily penetrates. Derivatives may also include those involving other reactive groups known to those skilled in the art. As used herein, the term "derivatives" includes metabolic precursors of lipoic acid. Where lipoic acid derivatives are employed, they must be functionally equivalent to lipoic acid. It is a further advantage of the invention that lipoic acid has beneficial properties for the treatment of skin damage, particularly inflammation and aging (U.S. Pat. No. 5,709,868 to Perricone), and also for the treatment of scars, particularly for hypertrophic and keloid scars (U.S. Pat. No. 5,965,618 to Perricone). In some typical embodiments, the composition contains from about 0.1% to about 7 weight %, lipoic acid, more narrowly from about 0.25% to about 5 weight %. In one embodiment, about 2% to 5% lipoic acid is employed.

Alpha-hydroxy acids are adjunct ingredients in many embodiments, alone or together with tyrosine and lipoic acid and those described below. As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are less bulky structurally so that they penetrate the skin well, and thus have a backbone of from one to three carbon atoms such as those more fully described in U.S. Pat. No. 5,965,618 to Perricone at column 6 lines 4 to 29. Where employed, glycolic and/or lactic acid or their derivatives are preferred; glycolic acid is especially efficacious. Glycolic acid or other α-hydroxy acids are typically present in amounts ranging from about 1% to about 10%, more narrowly from about 3% to about 7% of the total composition.

Fat-soluble fatty acid esters of ascorbic acid (vitamin C) are employed as an adjunct ingredient in other embodiments, alone or in combination with tyrosine, lipoic acid and/or α-hydroxy acids and folic acid described below. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. As is known by skilled workers, ascorbic acid esters include mono-, di-, tri- and tetraesters, and mixtures thereof. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize the alkanolamine in the composition. Ascorbyl palmitate and the like ascorbyl esters are typically present in amounts ranging from about 0.5% to about 15%, preferably from about 1% to about 7% to 10%, of the total composition. Vitamin A or vitamin A derivatives may be alternative or additional adjunct ingredients in like concentrations. Vitamin A and vitamin A derivates include, but are not limited to; retinol, retinyl palmitate, retinoic acid, retinal, and retinyl propionate.

Another adjunct ingredient useful in some compositions is folic acid. By "folic acid" is meant N-[4-[[(2-amino-1,4-dihydro-4-oxo-6-pteridinyl)methyl]amino benzoyl]-L-glutamic acid, also sometimes called pteroylglutamic acid, N-p-[[(2-amino-4-hydroxy-6-pteridinyl)methyl]amino]benzoyl]-glutamic acid, or N-(p-[(2-amino4-hydroxypyrimido[4,5-b]pyrazin-6-yl)methylamino]benzoyl-glutamic acid. Physiological salts of folic acid such as potassium or sodium salts and simple $C_1$ to $C_4$ esters may also be employed, provided that they exhibit the biological properties of folic acid. As used herein, when the term "folic acid" is used, it encompasses biologically equivalent derivatives. Typical folic or folate concentrations range between about 0.025% to about 1% by weight, more narrowly from about 0.05% to about 0.5% by weight.

Only effective amounts of alkanolamine compositions are needed to provide observable improvement in hair and nails when used alone, or in combination with other ingredients, so generally topical application is accomplished in association with a carrier, and particularly one in which the alkanolamine active ingredient is soluble per se or is effectively solubilized (e.g., as an emulsion or microemulsion). Where employed, the carrier is inert in the sense of not bringing about a deactivation or oxidation of the active ingredient(s), and in the sense of not bringing about any adverse effect on the skin areas to which it is applied. In one preferred practice of the invention, the active ingredients are applied in admixture with a dermatologically acceptable carrier or vehicle (e.g., as a lotion, cream, ointment, soap, stick, or the like) so as to facilitate application and, in some cases, provide additional therapeutic effects as might be brought about, e.g., by application to adjacent skin areas for the treatment of hair bulbs and paraungual nail matrix areas. While the carrier for dermatological compositions can consist of a relatively simple solvent or dispersant such as water, it is generally preferred that the carrier comprise a composition more conducive to topical application, and particularly one which will form a film or layer on the hair or nails to which it is applied so as to localize the application and provide some resistance to washing off by immersion in water and/or aid in penetration. Many preparations are known in the art, and include lotions containing oils and/or alcohols and emollients vegetable oils, hydrocarbon oils and waxes, silicone oils, animal or marine fats or oils, glyceride derivatives, fatty acids or fatty acid esters or. alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into nail coatings by utilization of different proportions of the ingredients and/or by inclusion of thickening agents such as gums or other forms of hydrophilic colloids. One preferred embodiment is a cleanser; another is a shampoo; and others are lotions, creams, and gels. Such compositions are referred to herein as dermally or dermnatologically acceptable carriers, and are formulated using conventional techniques known to those of ordinary skill in the art. A preferred application to hair is a rinse, though alkanolamines and adjunct ingredients may also be formulated as a shampoo. A preferred application to nails is a fingertip soak, but compositions may be painted on or applied as a lotion, cream or salve.

Suitable carriers include water, alcohols, oils and the like, chosen for their ability to dissolve or disperse active ingredients. Generally, even low concentrations of active ingredients in a carrier are suitable, depending upon the application regimen and the active and adjunct ingredients employed. Mild skin and hair conditions typically require lower concentrations of active ingredients than do acute conditions. As a practical matter, however, to avoid the need for repeated application, it is desirable that the topically applied composition be formulated to contain the amounts of active ingredients set out above. Generally in the practice of methods of the invention, the composition is applied to hair when it is shampooed and to nails when they are manicured, it generally being the case that gradual improvement is noted with each successive application. In so far as has been determined based upon clinical studies to date, no adverse side effects are encountered. It is an advantage of the invention that compositions of the invention do not require a pharmaceutical prescription.

Topical compositions of the invention can comprise additional ingredients commonly found in skin and hair care compositions, such as, for example, tinting agents, emollients, skin conditioning agents, emulsifying agents, humectants, preservatives, antioxidants, perfumes, chelating agents, etc., provided that they are physically and chemically compatible with other components of the composition. Preservatives include, but are not limited to, $C_1$–$C_3$ alkyl parabens and phenoxyenthanol, typically present in an amount ranging from about 0.5% to about 2.0% by weight percent, based on the total composition. Emollients, typically present in amounts ranging from about 0.01% to 5% of the total composition include, but are not limited to, fatty esters, fatty alcohols, mineral oils, polyether siloxane copolymers, and mixtures thereof. Humectants, typically present in amounts ranging from about 0.1% to about 5% by weight of the total composition include, but are not limited to, polyhydric alcohols such as glycerol, polyalkylene glycols (e.g., butylene glycol, propylene glycol, dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, and mixtures thereof. Emulsifiers, typically present in amounts from about 1% to about 10% by weight of the composition, include, but are not limited to, stearic acid, cetyl alcohol, stearyl alcohol, steareth 2, steareth 20, acrylates/$C_{10-30}$ alkyl acrylate crosspolymers, and mixtures thereof. Chelating agents, typically present in amounts ranging from about 0.01% to about 2% by weight, include, but are not limited to, ethylenediamine tetraacetic acid (EDTA) and derivatives and salts thereof, dihydroxyethyl glycine, tartaric acid, and mixtures thereof. Antioxidants, typically present in an amount ranging from about 0.02% to about 0.5% by weight of the composition, include, but are not limited to, butylated hydroxy toluene (BHT); vitamin C and/or vitamin C derivatives, such as fatty acid esters of ascorbic acid, particularly asocorbyl palmitate; butylated hydroanisole (BHA); phenyl-α-naphthylamine; hydroquinone; propyl gallate; nordihydroquiaretic acid; vitamin E and/or derivatives of vitamin E, including tocotrienol and/or tocotrienol derivatives; calcium pantothenates; green tea extracts; mixed polyphenols; and mixtures of any of these. As mentioned above, particularly preferred antioxidants are those that provide additional benefits to the scalp such as ascorbyl palmitate. (See additional ingredients and methods in U.S. Pat. Nos. 4,775,530, 5,376,361, 5,409,693, 5,545, 398, 5,574,063, 5,643,586, 5,709,868, 5,879,690, 5,965,618, 5,968,618, 6,051,244, 6,162,419, and 6,191,121 to Perricone).

Buffering agents are employed in many compositions. Preferably, the amount of buffering agent is one that results in compositions having a pH ranging from about 4.5 to about 8.5, more preferably from about 5.5 to about 8.5, most preferably from about 6.5 to about 8.0. Typical buffering agents are chemically and physically stable agents commonly found in cosmetics, and can include compounds that are also adjunct ingredients such as citric acid, malic acid, and glycolic acid buffers.

In a trial study, hair rinses formulated to contain 0.1% to 3% DMAE either in a phospholipid base, a cationic hair conditioner base, or a nonionic shampoo all out-performed the same hair care products without active ingredients in an open-ended, unblinded comparison of overall hair manageability, softness, and shininess. The effect was more pronounced in subjects with sun- and chlorine-bleached hair.

Fingernails of subjects who soaked the tips of one hand in a solution containing 3% DMAE and 5% tyrosine in a phospholipid base were less brittle and smoother than the fingernails of the other hand soaked in base only. The same effect was seen when the solution was applied topically to the nails or with a brush.

It an advantage of the invention that use of alkanolamine compositions provide a number of beneficial effects previously described and summarized above: alkanolamines advantageously quell inflammation, treat and prevent skin damage and aging (U.S. Pat. No. 5,554,647 to Perricone), increase subcutaneous muscle tone (ibid.), prevent and treat acne scars and other disfigurements, and cause visible contraction of skin pores, resulting in clearer, smoother appearing skin to areas drenched by compositions during hair treatments, to the scalp, and to paraungual areas around the nails, and stimulating better growth of the hair shaft and smoother, stronger nail plates. Beneficial effects are immediate, the results are cumulative, and formulations of the invention are well-tolerated by the skin and scalp. With continued applications, hair, nails, and surrounding skin areas are improved. It is another and important advantage of the invention already discussed that alkanolamines are antiinflammatories, and treat seborrhea and various types of dermatitis, decrease erythema in lesions and perilesional areas of persons having injured areas of the hands and scalp, as well as treating subclinical inflammations that adversely impact the formation of normal keratin in hair and nails. Taken together, all these effects increase the smoothness and surface uniformity of hair and nails, and the surrounding skin.

Treatment of hair with compositions of the invention, typically used as a shampoo or rinse, render hair softer, more manageable, and shiny, and the effect is pronounced in the treatment of sun- or chemically bleached hair, including chlorine-bleached hair, especially after treatments sufficiently long to promote better hair shaft growth. Magnification of individual treated hairs show visibly more intact keratin and smoother, less fragmented shanks than untreated controls. Application of alkanolamine compositions to nails results in their becoming more lustrous and considerably less brittle and pitted. Magnification of nail plates shows a better lamellar pattern with fewer pits. As summarized above, while not wishing to be bound by any theory, preferred compositions containing lipid penetrants seem to drive active ingredients into the hair shaft and nail surface, softening the keratin matrix, providing emolliency to the keratin and making it more elastic, while at the same time promoting better keratin production in the hair follicle and nail matrix. And, as has been mentioned, the effect is cumulative. Successive applications enhance the appearance of both hair and nails.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for treating hair or nails to render them more uniform and smoother comprising topically applying to the hair and underlying skin or nails and paraungual areas, a composition containing an effective amount of an alkanolamine of the formula

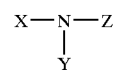

wherein X, Y and Z are selected from the group consisting of hydrogen, $C_1$–$C_3$ alkyl groups, $C_2$–$C_4$ alkanol group, wherein at least one of X, Y, or Z is a $C_2$–$C_4$ alkanol group bearing at least one hydroxyl group and optionally at least one carboxyl group.

2. A method according to claim 1 wherein the alkanolamine is selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

3. A method according to claim 2 wherein the alkanolamine is dimethylaminoethanol.

4. A method according to claim 2 wherein composition contains from about 0.1% to about 10% by weight alkanolamine.

5. A method according to claim 4 wherein the composition contains from about 1% to about 5% by weight alkanolamine.

6. A method according to claim 5 wherein the composition contains from about 2% to about 3% by weight alkanolamine.

7. A method according to claim 1 wherein the composition contains at least one adjunct ingredient selected from the group consisting of lipoic acid, tyrosine, an α-hydroxy acid, folic acid, an ascorbic fatty acid ester, and a mixture of any of these.

8. A method according to claim 7 wherein the composition contains from about 0.01% to about 6% tyrosine as an adjunct ingredient.

9. A method according to claim 7 wherein the composition contains from about 0.1% to about 7% by weight lipoic acid as an adjunct ingredient.

10. A method according to claim 7 wherein the composition contains from about 0.025% to about 1% by weight folic acid.

11. A method according to claim 7 wherein the composition contains from about 1% to about 10% by weight glycolic acid.

12. A method according to claim 7 wherein the composition contains from about 0.5% to about 15% ascorbyl palmitate.

13. A method for increasing the uniformity of keratin in hair or nails comprising applying to hair and its underlying skin or nails and paraungual areas a composition containing an effective amount of an alkanolamine selected from the group consisting of ethylaminoethanol, methylaminoethanol, dimethylaminoethanol, isopropanolamine, triethanolamine, isopropanoldimethylamine, ethylethanolamine, 2-butanolamine, choline, serine, and mixtures thereof.

14. A method according to claim 13 wherein the alkanolamine is dimethylaminoethanol.

15. A method according to claim 13 wherein the composition further contains an adjunct ingredient selected from the group consisting of lipoic acid, folic acid, tyrosine, ascorbyl palmitate, glycolic acid, and mixtures thereof.

16. A method according to claim 13 wherein the alkanolamine is present in the composition in an amount ranging from about 0.1% to about 10% by weight of the composition.

17. A method according to claim 16 wherein the adjunct ingredient is tyrosine.

18. A method according to claim 16 wherein the adjunct ingredient is lipoic acid.

19. A method of treating hair and nails to render them smoother and more uniform, to increase the emolliency of the keratin, and enhance hair and nail growth comprising topically applying to said hair and underlying skin and nails and paraungual areas a composition containing an effective amount of dimethylaminoalcohol and tyrosine.

20. A method according to claim 19 wherein the composition comprises about 0.1% to about 10% by weight dimethylaminoalcohol and 0.01% to about 6% by weight tyrosine.

* * * * *